United States Patent [19]

Kitzing et al.

[11] 4,287,348
[45] Sep. 1, 1981

[54] PREPARATION OF SULPHOALKYL QUATERNARY SALTS

[75] Inventors: Rainer Kitzing, Ingatestone; Geoffrey E. Ficken, Ilford; Victor W. Dolden, Romford, all of England

[73] Assignee: Ciba-Geigy AG, Basel, Switzerland

[21] Appl. No.: 912,702

[22] Filed: Jun. 5, 1978

[30] Foreign Application Priority Data

Jun. 10, 1977 [GB] United Kingdom ............... 24299/77

[51] Int. Cl.³ ................. C07D 293/12; C07D 277/62; C07D 263/54; C07D 235/04
[52] U.S. Cl. ..................................... 548/121; 548/100; 548/169; 548/179; 548/186; 548/203; 548/221; 548/217; 548/229; 548/230; 548/235; 548/329; 548/333; 548/337; 548/341; 260/326.12 R; 260/326.5 S; 260/326.9; 542/473
[58] Field of Search ............... 260/298, 302 R, 302 S, 260/302 S D, 304 R, 304 C, 304 D, 304 H, 306, 307 R, 307 C, 307 D, 307 F, 326.12 R, 326.5 SF, 326.9; 548/320, 333, 341, 100, 121, 169, 179, 186, 203, 221, 217, 229, 230, 235, 329, 37

[56] References Cited

U.S. PATENT DOCUMENTS

| 2,503,776 | 4/1950 | Sprague .................... 260/304 C X |
| 3,177,210 | 4/1965 | Rosenoff .................... 260/298 X |
| 3,274,204 | 9/1966 | Klass et al. ................. 260/294.8 S |
| 3,882,120 | 5/1975 | Piesch et al. ................ 548/320 X |

Primary Examiner—Donald G. Daus
Assistant Examiner—Diana G. Rivers
Attorney, Agent, or Firm—Sprung, Felfe, Horn, Lynch & Kramer

[57] ABSTRACT

Sulphoalkyl quaternary salts of the formula

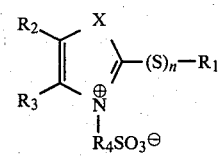

wherein X is —O—, —Se—, —S—, —NR— or —CR(-R)—, R is hydrogen or alkyl, $R_1$ is hydrogen, methyl or ethyl, $R_2$ and $R_3$ are each hydrogen or substituents or together represent the atoms necessary to complete an optionally substituted benzene ring, $R_4$ is optionally substituted alkylene of 3 or 4 carbon atoms and n is 1 or 0, except that when n is 1, $R_1$ cannot be hydrogen, are prepared by heating at a temperature above 80° C. a heterocyclic base of the formula

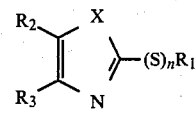

wherein X, $R_1$, $R_2$, $R_3$ and n have the indicated meanings with a hydroxysulphonic acid of the formula $HOR_4SO_3H$.

8 Claims, No Drawings

PREPARATION OF SULPHOALKYL QUATERNARY SALTS

This invention relates to the production of sulphoalkyl quaternary salts.

Sulphoalkyl quaternary salts are of use as intermediates in particular in the production of cyanine optical sensitising dyes.

In the past sulphoalkyl quaternary salts have been prepared using sultones (British Patent Specification No. 742,112) but recently it has been reported that the sultones exhibit carcinogenic properties and thus their industrial use is to be avoided. We have now discovered a new method of preparing sulphoalkyl quaternary salts without handling sultones.

According to the present invention quaternary salts of the general formula

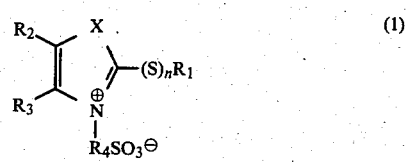  (1)

wherein X is —O—, —Se—, —S—, —NR— or —CR(-R)—, wherein R is alkyl of 1 to 4 carbon atoms or hydrogen, $R_1$ is hydrogen, methyl or ethyl, $R_2$ and $R_3$ are each hydrogen or substituent groups or together they represent the atoms necessary to complete an optionally substituted benzene ring and $R_4$ is an optionally substituted alkylene chain having 3 or 4 carbon atoms in the chain and n is 1 or 0, except that when n is 1, $R_1$ cannot be hydrogen, are prepared by heating at a temperature above 80° C. a heterocyclic base of the general formula

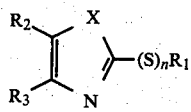  (2)

where X, $R_1$, $R_2$ and $R_3$ and n have the indicated meanings with a hydroxysulphonic acid of the general formula

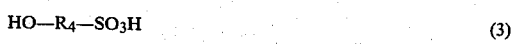

HO—$R_4$—$SO_3$H  (3)

where $R_4$ has the indicated meaning under conditions so that the water formed is removed from the reacting mixture.

$R_2$ and $R_3$ are hydrogen or e.g. alkyl or hydroxyalkyl of 1 to 4 carbon atoms, phenyl, or halogen such as chlorine or bromine or halogenated alkyl such as trifluoromethyl.

The water may be removed from the reaction mixture by causing it to distil from the reacting mixture or by carrying out the reaction in the presence of a solvent, e.g. xylene or 2-butoxyethanol, which forms an azeotrope with the water and is then removed also by distillation, or by carrying out the reaction in the presence of a compound able to combine with the water, e.g. acetic anhydride.

The invention is of particular use when the base of formula (2) is a heterocyclic base of the formula

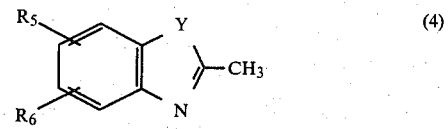  (4)

wherein Y is —Se—, —O— or —S— or —NR— and $R_5$ and $R_6$ represent hydrogen or substituents on the benzene ring, preferably methyl, ethyl, trifluoromethyl, chlorine, bromine or phenyl.

The sulphoalkyl substituted quaternary salt of compounds of formula (4) is the basis of a great many methinecyanine dyes. When such sulphoalkyl substituted quaternary salts of the compounds of formula (4) are prepared by the method of the present invention they need not be isolated from the reaction mixture and the requisite cyanine dye may be prepared from the reaction mixture and then isolated. An example of such a reaction is given in Example 1 which follows.

The hydroxysulphonic acids of use in the preparation of the present invention may be represented by the formula

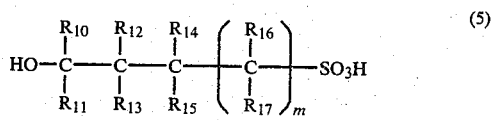  (5)

where m is 0 or 1 and each of $R_{10}$ to $R_{17}$ may be hydrogen or a substituent group selected from alkyl or aryl. Alternatively two adjacent carbon atoms in the alkylene chain may be part of a ring system. Hydrogen as radical $R_{10}$ to $R_{17}$ is preferred.

The following Examples will serve to illustrate the invention.

EXAMPLE 1

16.2 g of sodium 3-hydroxypropanesulphonate were converted into the free acid by treating the aqueous solution with an acidic ion-exchange resin (British Pat. No. 774,563). The resulting solution was evaporated to small volume, 16.4 g of 2-methylbenzothiazole and 100 ml of xylene were added, and the mixture was heated under reflux for 10 hours, the water being removed continuously. The xylene was poured off from the resulting brown solid, which was purified by refluxing with acetone.

The quaternary salt so obtained was not purified further, but was dissolved in a mixture of methanol and acetonitrile and treated with 3-ethyl-2(2-chloropropenyl)benzthiazolium chloride and triethylamine as condensing agent to give the dye anhydro-(3-ethyl-2-benzothiazole)-[3-(3-sulphopropyl-2-benzothiazole)]-β-methyltrimethinecyanine hydroxide in 45% yield overall on the sodium salt.

In a similar manner, 2,5,6-trimethylbenzothiazole gave a quaternary salt which was converted into anhydro(3-ethyl-2-benzothiazole)-[5,6-dimethyl-3-(3-sulphopropyl)-2-benzothiazole]-β-methyltrimethinecyanine hydroxide.

EXAMPLE 2

15.4 g of 4-hydroxybutanesulphonic acid and 22.8 g of 1-ethyl-2-methyl-5-trifluoromethyl benzimidazole were heated together in an oil-bath at 150° C., the water formed being caused to distil out. The cooled product was boiled with 100 ml of acetone, filtered off, and crystallized from 100 ml of ethanol. The anhydro-1-ethyl-2-methyl-3-(4-sulphobutyl) 5-trifluoromethylbenzimidazolium hydroxide was obtained as a colourless solid, m.p. 285°–287° C. (decomposition). The yield was 8.3 g (23%).

EXAMPLE 3

(a) A mixture of 7.45 g of 2-methylbenzothiazole, 7.0 g of 3-hydroxypropanesulphonic acid, and 2.3 ml of acetic anhydride were heated in an oil-bath at 175° C. for 5 hours. The cooled product was refluxed with 100 ml of acetone, the acetone solution was poured off, and the residue was crystallised from a mixture of ethanol and acetone. By this means, 5.9 g (44%) of anhydro-2-methyl-3-(3-sulphopropyl)-benzothiazolium hydroxide, m.p. 283°–284° C. (decomposition) was obtained.

(b) Using a similar procedure, the following quaternary salts were produced:

| Quaternary salt | Yield (%) | M.p. |
| --- | --- | --- |
| Anhydro-5-bromo-2-methy-3-(3-sulphopropyl)-benzothiazolium hydroxide | 42 | 296–297° C. |
| Anhydro-5-bromo-2-methyl-3-(3-sulphobutyl)-benzothiazolium hydroxide | 12 | 253–254° C. |
| Anhydro-2-methyl-4,5-diphenyl-3-(3-sulphopropyl)-thiazolium hydroxide | 38 | 254–256° C. |
| Anhydro-2-methyl-5-phenyl-3-(3-sulphopropyl)-benzoxazolium hydroxide | 79 | 140–145° C. |
| Anhydro-2,5,6-trimethyl-3-(3-sulphopropyl)-benzoselenazolium hydroxide | 30 | 225–230° C. |

EXAMPLE 4

A mixture of 9.25 g of 2-methylbenzothiazole hydrochloride and 8.9 g of potassium 3-hydroxypropanesulphonate was heated at 175° C. for 1½ hours with occasional stirring. The cooled product was boiled with 50 ml of methanol and filtered hot, and the residue was extracted similarly with a further 25 ml of methanol. The combined filtrates were cooled and treated with ether to precipitate anhydro-2-methyl-3-(3-sulphopropyl)-benzothiazolium hydroxide (6.6 g, 49%), identical with that prepared as in Example 3(a).

EXAMPLE 5

A solution of 17.9 g of 2-methylbenzothiazole in 50 ml of 2-butoxyethanol was heated to boiling in a flask fitted with a short fractionating column. A solution of 14.0 g of 3-hydroxypropanesulphonic acid in 25 ml of methanol was added over 1 hour, water and methanol being distilled out continuously. When addition was complete, heating was continued until the b.p. reached 168° C. The cooled solution was treated with ether, to precipitate the crude quaternary salt, which was purified as in Example 3(a). The yield of anhydro-2-methyl-3-(3-sulphopropyl)-benzothiazolium hydroxide was 1.8 g (7%).

What we claim is:

1. A process for the preparation of quaternary salts of the general formula

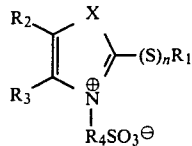

wherein X is —O—, —Se—, —S—, —NR— or —CR(R)—, wherein R is alkyl of 1 to 4 carbon atoms or hydrogen, $R_1$ is hydrogen, methyl or ethyl, $R_2$ and $R_3$ are each hydrogen, alkyl or hydroxyalkyl of 1 to 4 carbon atoms, phenyl, halogen or halogenated alkyl or together they represent the atoms to complete a benzene ring which is unsubstituted or substituted by methyl, ethyl, trifluoromethyl, chlorine, bromine and or and $R_4$ is an alkylene chain having 3 or 4 carbon atoms in the chain and n is 1 or 0, except that when n is 1, $R_1$ cannot be hydrogen, which comprises heating at a temperature above 80° C., a heterocyclic base of the general formula

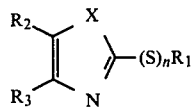

where X, $R_1$, $R_2$ and $R_3$ and n have the indicated meanings with a hydroxysulphonic acid of the general formula

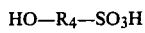

HO—$R_4$—SO$_3$H where $R_4$ has the indicated meaning under conditions so that the water formed is removed from the reacting mixture.

2. A process according to claim 1, wherein the water is removed from the reaction mixture by causing it to distil from the reacting mixture.

3. A process according to claim 1, wherein the water is removed from the reaction mixture by carrying out the reaction in the presence of a solvent which forms an azeotrope with the water and is then removed by distillation.

4. A process according to claim 3, wherein the solvent which forms an azeotrope with the water is xylene or 2-butoxyethanol.

5. A process according to claim 1, wherein the water is removed from the reaction mixture by carrying out the reaction in the presence of a compound able to combine with the water.

6. A process according to claim 5, wherein the compound able to combine with the water is acetic anhydride.

7. A process according to claim 1, wherein the heterocyclic base is of the formula

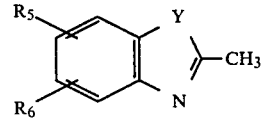

wherein Y is —Se—, —O— or —S— or —NR— and $R_5$ and $R_6$ represent hydrogen, methyl, ethyl, trifluoromethyl, chlorine, bromine or phenyl.

8. A process according to claim 1, wherein the hydroxysulphonic acid is of the formula

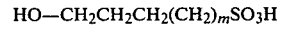

HO—CH$_2$CH$_2$CH$_2$(CH$_2$)$_m$SO$_3$H where m is 0 or 1 and each of $R_{10}$ to $R_{17}$ is hydrogen.

* * * * *